(12) United States Patent
Alhussiny

(10) Patent No.: US 10,485,440 B2
(45) Date of Patent: *Nov. 26, 2019

(54) HEART MONITOR ELECTRODE SYSTEM

(71) Applicant: Global Cardiac Monitors, Inc., Sugar Land, TX (US)

(72) Inventor: Karim Alhussiny, Houston, TX (US)

(73) Assignee: Global Cardiac Monitors, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/974,624

(22) Filed: May 8, 2018

(65) Prior Publication Data
US 2018/0256062 A1  Sep. 13, 2018

Related U.S. Application Data

(63) Continuation of application No. 12/012,958, filed on Feb. 6, 2008, now Pat. No. 9,962,098, which is a continuation-in-part of application No. 12/006,907, filed on Jan. 7, 2008, now abandoned, which is a continuation of application No. 11/810,031, filed on Jun. 4, 2007, now abandoned.

(60) Provisional application No. 60/810,743, filed on Jun. 2, 2006.

(51) Int. Cl.
*A61B 5/04* (2006.01)
*A61B 5/0408* (2006.01)

(52) U.S. Cl.
CPC .. *A61B 5/04085* (2013.01); *A61B 2560/0412* (2013.01)

(58) Field of Classification Search
CPC ............... A61B 5/04085; A61B 2560/0412
See application file for complete search history.

(56) References Cited

U.S. PATENT DOCUMENTS

2006/0085049 A1* 4/2006 Cory ................... A61B 5/0536
607/48

* cited by examiner

*Primary Examiner* — Catherine M Voorhees
*Assistant Examiner* — Natasha Patel
(74) *Attorney, Agent, or Firm* — Gordon G. Waggett, P.C.

(57) ABSTRACT

A bioelectric interface for monitoring, detection and transmission of detected ECG data is provided comprising a sensory system for detecting bio-physiological measurements utilizing spatially resolved potential profiles obtained from a localized cluster of sub-electrodes to form constituent sets of miniature sensor arrays. Using only a single macro-electrode, two or more sets of sub-electrode arrays are used to measure bipolar spatial gradients obtained from measured cardiac potentials. The sets of sub-electrodes containing the clusters are optimized to attain measurable gradients of diagnostic value. A minimax procedure allows bio-potential sensory acquisition through a bi-directional digital steering process, which essentially comprises monitoring, detection, selection, grouping, recording and transmission of ECG waveform characteristic data.

15 Claims, 3 Drawing Sheets

Heart Monitor Electrode Structure - Concept of Islands

Side View of the Electrode ═══→ Lead

Normal Leads

Leads belonging to Island 1 (cluster1)

Leads belonging to Island 2 (cluster2)

Leads belonging to Island 3 (cluster3)

HEART MONITOR ELECTRODE SYSTEM

CROSS-REFERENCE TO RELATED APPLICATIONS

The present application is a continuation of U.S. Nonprovisional application Ser. No. 12/012,958 filed Feb. 6, 2008, now U.S. Pat. No. 9,962,098, which is a continuation-in-part of U.S. Nonprovisional application Ser. No. 12/006,907, filed Jan. 7, 2008, now abandoned, which is a continuation of U.S. Nonprovisional application Ser. No. 11/810,031, filed Jun. 4, 2007, now abandoned, which claims the benefit of U.S. Provisional Application No. 60/810,743, filed Jun. 2, 2006, the disclosures of which are incorporated herein in their entireties.

COPYRIGHT AUTHORIZATION

©2008-2018 Global Cardiac Monitors, Inc. A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

STATEMENT REGARDING FEDERALLY SPONSORED RESEARCH OR DEVELOPMENT

Not Applicable.

BACKGROUND OF THE INVENTION

Field of the Invention

The present invention relates generally to the fields of bio-potential sensory measurements and transmission thereof for medical diagnostic purposes, and in a specific though non-limiting embodiment, to a comfortable, easily-affixable, portable bioelectric interface used to detect, monitor and communicate data relating to a subject patient's ECG waveform characteristics.

Description of the Related Art

Although well-known for over a century, the full benefit of the diagnosis of electrocardiogram recordings has not been realized, primarily because it has not yet been brought to the state of full clinical exploitation such technology deserves. Possible reasons for this shortfall include institutional resistance to sophisticated new electronics capable of subsuming the functions of many previously existent devices; misperceptions within the medical community regarding the possible uses of such systems when the technology is fully•matured; the fact that few, if any, prototypical devices have been reduced to practice for experimentation, etc.

The net result of such reluctances has been to restrict the proliferation and effectiveness of ECG monitoring systems to clinics, hospitals, and emergency rooms. More effective functionality, such as auto-detection, wireless transmission, and ultimate ease of usage, has heretofore been unknown.

For example, the state of the art presently is to affix upon a subject an electrocardiogram recording system based on measurement of the potential difference from at least a pair of electrodes that are•distinctly separated, and which connect with leads that terminate in the amplification stage. Examples of standard lead systems include the signal averaging x, y, z Frank set, and the 10 electrode averaging systems derived from the well-known, clinically standard 12 lead system. In virtually all cases, the electrodes are connected with wire leads to either an amplifier or a recording device.

It is problematic, however, that when affixing subjects with the standard 12-lead monitoring system, subjects must be affixed with all of the electrodes disposed in a proper anatomical position. Failure to so equip the subject results in either failure or poor reporting of the apparent ECG waveform.

Even when proper anatomical disposition is achieved, orientation and grouping of disjunctive constituent clusters is adversely influenced by the orientation of the myocardium muscle fibers with respect to the aspect of the cumulatively resulting solid angle obtained from a set of the electrodes. With respect to the sequence of activation, the spread of the activation stimulus moves from endocrinal sites on out to the transmural space. This space is heavily affected by the anisotrophic properties of the ventricular muscle.

It is intuitive that excitation or the wavefront will spread more rapidly along the long axes of the cardiac cell than in the transverse direction. In ventricular walls, fibers are oriented roughly parallel to both endocardial and epicardial surfaces, however there are some transverse connections between cells, therefore the spread from one endocardial point may be viewed as oblique. This means there is a predominant axial spread along the length of the fiber with a lesser degree of spread or activation along the transverse in the perpendicular direction. The cumulative effects of the resulting cardiac field manifest into corresponding deviations in the measured cumulative waveform. In short, measuring errors translate into analytical errors, which are then compounded during the amplification and recording process. The net result is that a testing protocol designed to be exacting and precise is not, much to the detriment of cardiac patients and their attending physicians.

It is also problematic that the wire leads associated with the electrodes more or less requires that the subject be confined and remains relatively still, and the lack of reliable remote reporting capability ensures that the subject must remain on-site during cardio interrogation. Consequently, benefits that could otherwise have been derived from the remote acquisition, transmission, and interpretation of waveform characteristics are not realized.

Several derivative electrode arrangements (for example, large patches) have been proposed as an alternative to the clinical standard. However, the basic challenge remains that such electrodes must be contiguous and sufficiently spatially separated. To avoid that fundamental necessity, prior arts have attempted and demonstrated embedded wires disposed in a lamination in various arrangements. However, the obstacle remains that these electrodes are contained within a relatively larger patch in which electrodes still have to be connected by wires disposed at relatively large spatial distances.

Accordingly, the prior art is deficient in achieving a clinically useful diagnostic potential gradient from a single electrode comprising a plurality of sub-clusters subtending and delimiting an area of no more than a few of inches or less.

Logical protocols, functional depictions, and satisfactory methodologies (i.e., decision rules) for constructing waveforms obtained from two or three sets of selected sub-clusters disposed in specific orientations, whether contiguous or disjointed, and grouping strategies for determining optimum signal acquisition, are also conspicuously absent.

SUMMARY OF THE INVENTION

A method of obtaining local gradient values from a bio-potential source for the purpose of cardiac monitoring is provided, wherein the method includes parsing of data obtained from clusters of sub-electrodes disposed on a single macro electrode.

An on-board electrode signal acquisition system is also provided, wherein the system includes filtering and processing capabilities, and wherein an associated dynamic range is set to a sufficiently broad range as to accommodate excursions intended to define baseline boundaries.

An ECG system in which a macro electrode having a plurality of sub-electrodes is combined with leads combined with a plurality of additional macro electrodes is also provided, wherein one or more of the additional macro electrodes further include a plurality of sub-electrodes.

A method of networking an ECG monitoring system which includes a master electrode is also provided, wherein remote interrogation of the monitoring system is carried out using voice data digital signal packaging.

DETAILED DESCRIPTION OF THE INVENTION

1. As mentioned, rudimentary patches and electrode clusters for clinical electrocardiography have been proposed and described in the prior art. However, the prior art has not understood and correctly manipulated several major principals in biopotential sensing paramount for sensitivity, spatial resolution, and correct orientation of electrodes within clusters comprising sub-electrodes confined to a relatively small zone.

Figure 1:
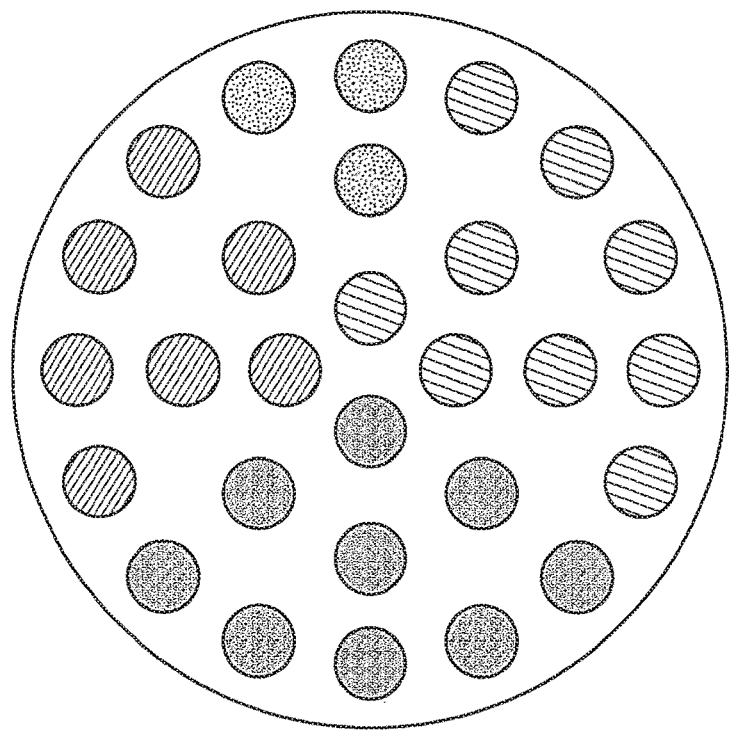
FIG. 1 depicts an overhead and side view of a heart monitor electrode structure.
Figure 1:
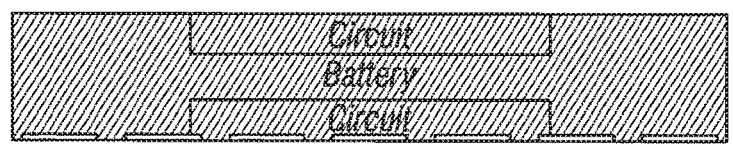
Figure 1:
Figure 1:
Figure 1:
Figure 1:
Figure 2:
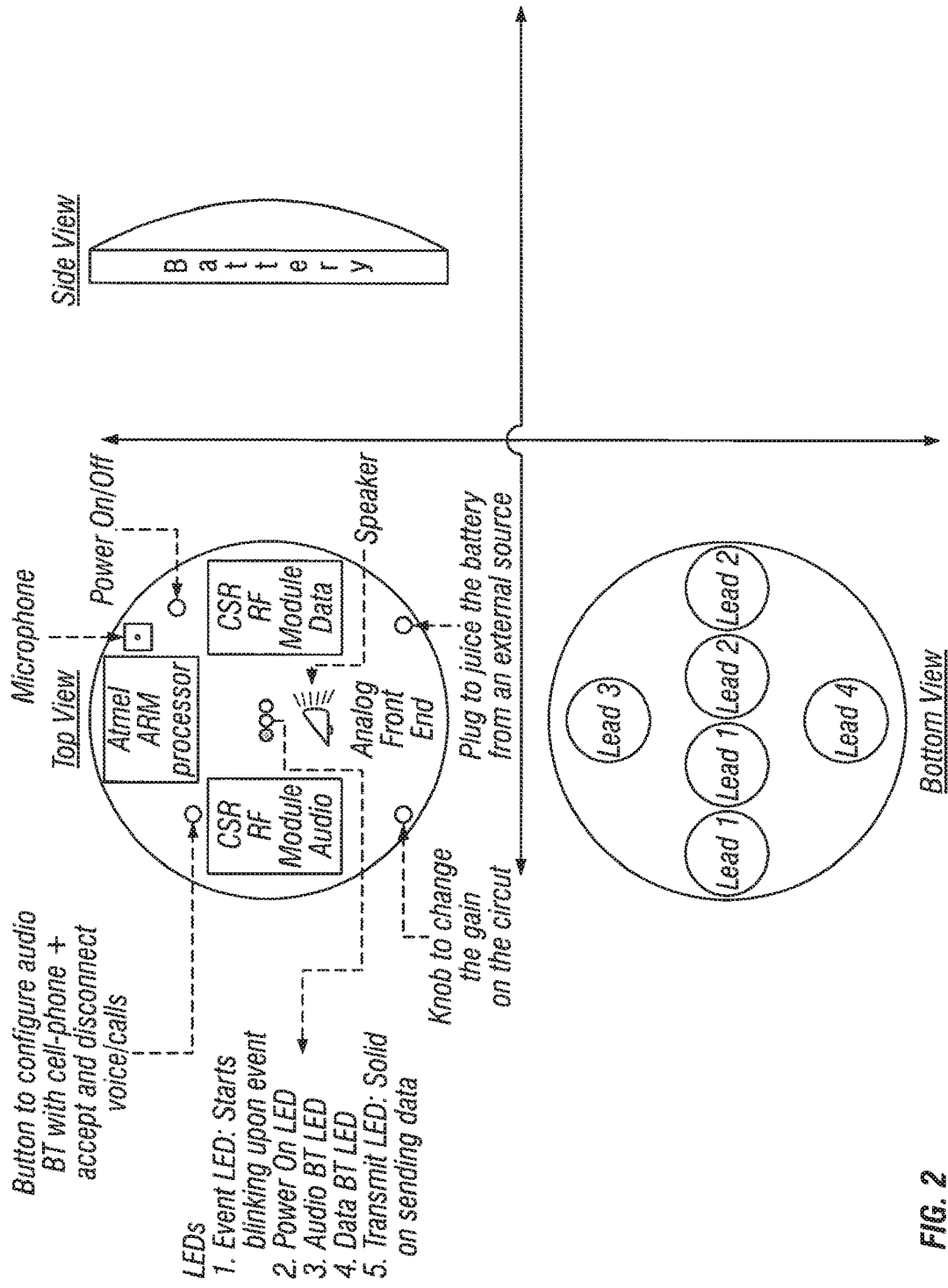
FIG. 2 depicts overhead, underneath, and cutaway views of the presently claimed heart monitor.

These principals are:

(A) A single electrode sensor array used to spatially resolve highly localized gradient profiles from a cluster of sub-electrodes to form constituent sets comprising subelectrodes under a specific decision rule. Such clusters will provide a minimum of two constituent, though not necessarily contiguous, sets obtained from members of the cluster to discern a measurable potential difference. See FIGS. 1 and 2.

(B) A so-called "minimax" procedure that allows for bio-potential sensory acquisition through a digital steering process, in which monitoring, selecting, grouping, recording and transmission options are derived from permutations of a plurality of sub-electrodes confined to the size of the typical ECG electrode.

(C) Potential contributions from all possible permutations of the cluster of subelectrodes combined and parsed into two or three macro constituent sets.

(D) A rotational invariance property resulting from the virtual steering of subelectrodes within cluster(s) to obtain measurable potential difference.

(E) A battery structure that provides power to both the body of the electrode and its sensor array. Power is also required for whatever extent of processing and transmission functions are carried out onboard the device, and to transmit raw data for processing to an associated, proximately disposed processor device, for example, remote processor worn by the subject in a harness.

Figure 3:
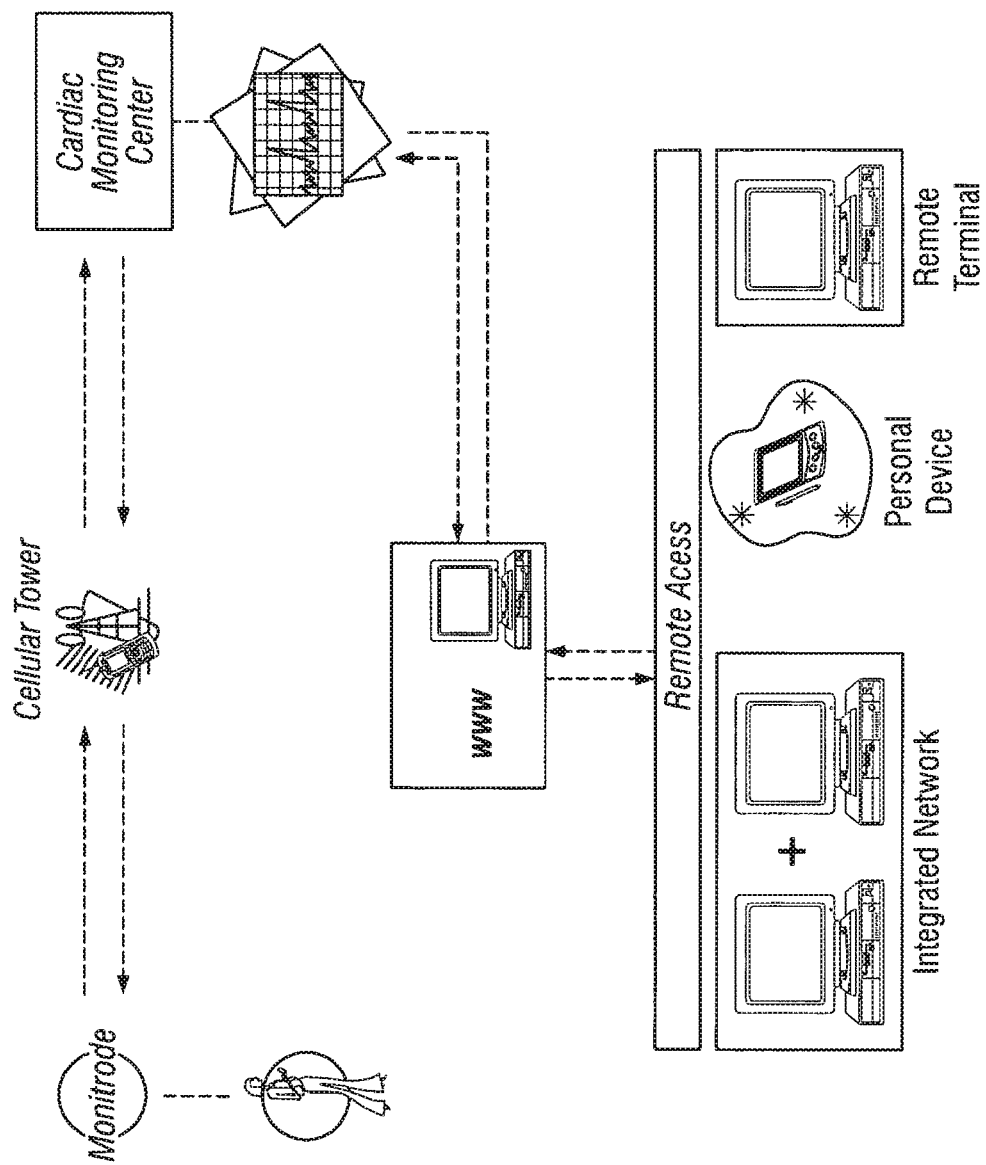
FIG. 3 illustrates examples of the remote transmission, monitoring and interrogation aspects of the presently claimed heart monitoring system.

(F) A wireless topology network model, wherein a remote monitor can interrogate the portable electrode unit. See FIG. 3.

(G) A distinct single electrode that is autonomous and lead-free, thereby achieving single electrode results with onboard DSP in association with arrhythmia detection capabilities, source encoding, and passive and active wireless transmission.

Consequently, the claimed invention essentially includes a data acquisition system capable of acquiring ECG data in association with a useful memory and a logical analytic protocol. Further aspects comprise a full duplex transmitter and receiver disposed, either onboard or in close physical proximity therewith (for example, contained within an associated portable harness or the like) in electrical communication with a structurally integral unit comprising a single electrode and a battery on an area spanning less than or approximately the same area as a typical electrode used in the presently known 12 lead clinical system.

2. The aforementioned sub-electrode data acquisition system comprises elements of:

(A) a bio-potential interface having a sensor array comprising a plurality of sub-electrode clusters integrated into a single system used to obtain gradient indicators obtained from highly localized potential differences; (B) a plurality of sub-electrode sets spatially parsed and in accord with a minimax method adapted to each individual subject patient in order to align sub-electrodes constellations in a manner so as to attain a measurable divergence between and amongst cardiac field force vectors; (C) an accumulated history of each patient's electrophysiological activity for purposes of arrhythmia detection and monitoring; and (D) a wireless network methodology used to maintain connectivity and assist with remote physician interrogation during critical sessions:

3. For clarity, it will probably be useful to note the following definitions employed throughout the balance of this disclosure:

(A) As used herein, the term "constituent sets" refer to either the 2 set model or the 3 set model of sub-electrodes, which, in the three set model constitute an exploring set, a reference set, and a ground set. In the two set model, the reference set is not present.

(B) The term "model" refers to either of 2 or 3 set clusters.

(C) The term "critical session" refers to a phase wherein an event of cardiac significance has been detected and stored, and is either awaiting transmission or is already in the process of being transmitted for analysis. Regarding "awaiting transmission," it is possible that a brief delay could be incurred due to, for example, a wireless network delay, etc.

(D) The term "measurable" refers to any detectable•potential derived from any diagnostic value obtained from waveform excursions.

(E) The term "enclosure model" refers to a structural embodiment wherein a battery is either or partially enclosed.

4. One aspect of the invention utilizes temporal and spatial-resolved detection of bio-physiological potential to obtain discernible waveforms from highly localized clusters of dry, gel, or suction cup electrodes from a body surface or from organs for diagnostic purposes. A related diagnostic procedure comprises a method in which the utility of a minimum of a single electrode is used to detect, as an example of one embodiment, the cardiac electrical disturbance. Drawing upon and recognizing the fundamentals of electrochemical processes that precipitate the various phases of action potential during the cardiac cycle, as well as the spatial and temporal correlations of associated individual and epidemiological data, reasonable inferences can be made as to the spatial and temporal gradient divergence and its spectra: Selection and formation of particular constellations are dictated by those sub-electrodes disposed coincident and subjacent to the sub-potential contours of high divergence during the cardiac cycle, thereby contributing the most to a measurable differential waveform.

Cardiac potentials sensed on body surfaces emanate as the result of a cardiac electric field interacting with metallic or gel electrodes affixed on the body surface. Thus, an electrode is essentially a transducer for transforming charges in electrolytes, i.e., anions and cations, into electrons (and vice versa) in metals in electronic circuits. With the aid of electrochemical gradients in the intra- and extra-cellular spaces, anions and cations are moved with the assistance of what is essentially a perpetual sodium pump that energizes the cell, thereby causing the action potential to travel through the conduction system of the myocardium. Conduction and displacement of capacitive currents flow across from cell to cell, entering and exiting through the cell membranes, in order to eventually activate and contract the ventricle pump. Electromagnetic fields from the activated myocardium project outwardly where subtending electrodes intercept that can be sensed as bio-potential on the body surface and then recorded.

The fundamental requirement of attaining a discernible gradient from a single electrode comprising clusters of N number of sub-electrodes in a highly localized potential warrants transition to the presently claimed technology.

Joint adaptive capabilities at the circuit level, e.g., joined elements such as capacitors and resistors, as well as digital processing permit iso-potential lines or contours to dictate the specific orientation of the sub-electrodes, and the subtending of clusters of sub-electrodes, to attain the said desired diagnostic gradient. The clusters or constellations of sub-electrodes, and of the resulting sets of such, need not be contiguous or uniform relative to one another, nor should they be exhaustive of all of the N sub-electrodes coincident to subjacent fibers to reveal the nature and extent of potential variability during the cardiac cycle.

5. Decision Rules

In one embodiment, all sub-electrodes present in the system terminate into a logical device, such as an addressable multiplexer, and the signals obtained from the electrodes are processed in accord with instructions from a microprocessor, digital signal processor (DSP), or any other suitable digital processor. Various sub-electrodes are combined into prospective sets to form the minimum necessary 2 or 3 constituent sets described above. These sets represent the potential points to obtain spatial/temporal waveform excursions, and are reflective of the cardiac signal that is preferably least noisy. The sets of clusters of sub-electrodes produce an effective orientation of highly localized bipolar arrangements that are then parsed in such a manner so as to discern or maximize the signal gradient associated with the least interference noise.

The selection of the 2 or 3 set clusters of sub-electrodes need not be dependent upon a contiguous grouping of clusters, though such disposition certainly can provide a maximum potential gradient with some sense of optimality if necessary. One possible optimality rule would be to combine sub-electrodes to contribute to a stable gradient, preferably of some visually desired display that is free or indiscernibly tolerable of AC interference, for example. Disposed on-board the master electrode module, or at minimum in electrical communication therewith, is a set of amplifiers and an addressable multiplexer used to communicate data regarding each all of the potential permutations obtained from the sub-electrodes to a signal processor or the like. The set of amplifiers is also used to assist in the selection of localized candidate clusters from amongst the possible spectrum of sub-electrode candidate clusters. The master electrode module can also be used as a hub for other master electrodes, thereby effectively forming a system of such master electrodes analogous to the standard electrode arrangements already known. In this case, each of the master electrodes, which would take the place of one of the simple, basic electrodes presently used in the standard system, would provide a significantly more accurate representation of actual cardio activity than would the standard clinical system.

The orientation selection process may exhaustively consider all possible combinations of sub-electrodes, or may instead continue only until a desired bipolar potential is attained. In some embodiments, the primary criterion is that maximum number of ECG excursions that both fall into the ECG band and are void of AC interference. A ground electrode may be necessary in certain embodiments, but in others only two electrode sets, each of which contain at least one sub-electrode, will suffice for obtaining the desired diagnostic EGG signal.

The method herein described thus obtains electro-potential data from each of the leads of the heart monitor, determines which leads have the maximum potential difference, and uses that maximum potential difference as the heart monitoring data, using maximum potential for monitoring data enhances the data readability and reliability.

In short, the minimax algorithm isolates and considers a minimum of two constituent sets selected from members of the cluster in order to discern measurable potential differences. Potential from all possible permutations of the cluster constituting at least two sets of sub-electrodes are combined, and then parsed into two or three macro constituent sets or constellations. Each set can have a minimum of one sub-electrode. A distinct lead-free single electrode that is rotationally invariant results with onboard DSP for arrhythmia detection, source encoding, and passive and active wireless transmission.

This lead-free, bio-physiological adapter allows for utmost clinical operational freedom and dramatically obviates the need for leads of any length that invariably encumber the acquisition and performance of ECG recordings as presently performed.

6. Conclusion

The foregoing specification is provided for illustrative purposes only, and is not intended to describe all possible aspects of the present invention. Moreover, while the invention has been shown and described in detail with respect to several exemplary embodiments, those of ordinary skill in the pertinent arts will appreciate that minor changes to the description, and various other modifications, omissions and additions may also be made without departing from either the spirit or scope thereof.

I claim:

1. A non-invasive method of obtaining local gradient values from a bio-potential source for the purpose of biophysiological signal monitoring by affixing a lead-free, autonomous single macro electrode, without regard to anatomical orientation, to a body surface of a subject to be monitored, the macro electrode comprising a group of N number of sub-electrodes, namely, two or more sub-electrodes arranged in a highly localized constellation capable of detecting highly localized, closely spaced biophysiological electrical potential gradients between two or more constituent sets of the sub-electrodes, each set of sub-electrodes comprising at least one distinct sub-electrode of the two or more sub-electrodes; acquiring the biophysiological signal from two or more of the sub-electrodes within the constellation; parsing data obtained from all sub-electrodes disposed upon the single macro electrode with a microprocessor disposed in communication therewith; determining with said microprocessor a set of sub-electrodes that contributed to the maximum local gradient according to the anatomical orientation of the macro electrode on the body surface of the subject; and wirelessly transmitting the determined maximum local gradient, wherein the macro electrode is affixed to the body surface of the subject without regard to rotational orientation of the macro electrode.

2. The method of claim 1 further comprising the step of remote interrogation of the macro electrode carried out using voice data digital signal packaging.

3. The method of claim 2, wherein said remote interrogation of the macro electrode discerns data relating to biophysiological phenomena occurring in muscle tissue.

4. The method of claim 1, wherein the biophysiological signal originates from the subject's heart.

5. The method of claim 1 further comprising the steps of parsing the data from all of the sub-electrodes; determining which of the sub-electrodes, either alone or in combination with another sub-electrode or other sub-electrodes or a combination of other sub-electrodes, provide a maximum gradient value when contrasted against said another sub-electrode or said other sub-electrodes or said combination of sub-electrodes; and using the so determined maximum gradient value for the purpose of the biophysiological signal monitoring.

6. The method of claim 5 wherein the steps of parsing are conducted using a minimax procedure adapted to each individual subject to be monitored in order to align sub-electrodes in a manner so as to attain a measurable divergence between and amongst biophysiological signals.

7. The method of claim 5 wherein the steps of parsing are conducted using a minimax procedure that allows for bio-potential sensory acquisition through a digital steering process, in which monitoring, selecting, grouping, recording and transmission options are derived from permutations of a plurality of the sub-electrodes.

8. The method of claim 5 wherein the sub-electrodes subtend and delimit an area of no more than a few of inches or less.

9. The method of claim 5 wherein the steps of parsing occur on a temporal and spatial basis.

10. A system for obtaining biophysiological sensory measurements from a subject, in which a lead-free, autonomous single macro electrode having a plurality of sub-electrodes arranged in a highly localized constellation capable of detecting highly localized, closely spaced biophysiological electrical potential gradients between two or more constituent sets of the sub-electrodes, each set of sub-electrodes comprising at least one distinct sub-electrode of the two or more sub-electrodes, is combined with leads combined with a plurality of additional macro electrodes, one or more of which also further comprise a plurality of sub-electrodes, the macro electrodes being affixed, without regard to anatomical orientation, to a body surface of the subject, the system further comprising a microprocessor disposed in communication therewith, the system capable of acquiring the biophysiological signal from two or more of the sub-electrodes within the constellation, parsing data obtained from all sub-electrodes disposed upon the single macro electrode with said microprocessor, and determining, with said microprocessor, a set of sub-electrodes that contributed to the maximum local gradient according to the anatomical orientation of the macro electrode on the body surface of the subject; wherein the macro electrode is affixed to the body surface of the subject without regard to rotational orientation of the macro electrode, and wherein said system is capable of wirelessly transmitting the determined maximum local gradient.

11. The system of claim 10 further comprising an on-board electrode signal acquisition system, wherein said signal acquisition system comprises filtering and processing capabilities, and wherein an associated dynamic range is set to a sufficiently broad range as to accommodate excursions intended to define baseline boundaries.

12. The system of claim 10, wherein said microprocessor further comprises an adaptive algorithm comprising logic and a decision rule useful for enabling adjustment of parameters for acquiring bio-potential measurements.

13. The system of claim 10, further comprising a source encoder used to reduce the size of a digital representation of measured bio-potential.

14. The system of claim 10, further comprising a battery disposed within an enclosure in such a manner said battery can be extricated out of, and then a replacement battery wedged back into said enclosure.

15. The system of claim 10, wherein the system measures biophysiological sensory signals originating from the subject's heart.

* * * * *